US00PP29048P3

(12) United States Plant Patent
Southwick

(10) Patent No.: US PP29,048 P3
(45) Date of Patent: Mar. 6, 2018

(54) CHERRY TREE NAMED 'SMS-16-CA 2014-16'

(50) Latin Name: ***Prunus avium* L.**
Varietal Denomination: SMS-16-CA 2014-16

(71) Applicant: Stephen M. Southwick, Lodi, CA (US)

(72) Inventor: Stephen M. Southwick, Lodi, CA (US)

(73) Assignee: SMS Unlimited, LLC, Lodi, CA (US)

( * ) Notice: Subject to any disclaimer, the term of this patent is extended or adjusted under 35 U.S.C. 154(b) by 0 days.

(21) Appl. No.: 14/999,988

(22) Filed: Jul. 22, 2016

(65) Prior Publication Data

US 2018/0027711 P1 Jan. 25, 2018

(51) Int. Cl.
*A01H 5/08* (2006.01)

(52) U.S. Cl.
USPC ..... Plt./181
CPC ..... *A01H 5/085* (2013.01)

(58) Field of Classification Search
USPC ..... Plt./181
CPC ..... A01H 5/085; A01H 5/0216; A01H 5/08; A01H 5/0837
See application file for complete search history.

(56) References Cited

U.S. PATENT DOCUMENTS

PP6,676 P * 3/1989 Hansche ..... Plt./181

* cited by examiner

*Primary Examiner* — June Hwu
(74) *Attorney, Agent, or Firm* — Randall Danskin P.S.

(57) ABSTRACT

A new and distinct variety of cherry tree, which is denominated varietally as 'SMS-16-CA 2014-16' is described, and which produces fruit having a very large size, an early ripening time, is highly productive, and which further has symmetrically shaped fruit when grown under the ecological conditions prevailing in the states of California and Washington, and wherein the mature fruit displays little or no indentation along the suture line.

4 Drawing Sheets

Latin name: *Prunus avium* L.
Varietal denomination: 'SMS-16-CA 2014-16'.

BACKGROUND OF THE INVENTION

The new variety was discovered from an open pollination of seeds collected from a proprietary sweet cherry selection 'SC3-35' (unpatented), and which was located near Vina, Lodi, and Bakersfield, Calif. in 1998. The seeds stratified, testa removed, and then were germinated and planted in pots in 1999. After germination, the aforementioned seeds were grown in pots for 3 years until flowering. Fruit was first observed in 2002. A first asexual propagation took place when buds were taken in that same year and propagated on the *Prunus mahaleb* rootstock (unpatented) for further confidential trials, and which were conducted in Vina, Calif., and Spain starting in 2003. After two years of cropping in pots, buds were taken in a second asexual reproduction and grafted onto *Prunus mahaleb* rootstock for further evaluation in Stockton, Calif. in 2004. Additional confidential trials similar to that which are described, above, were conducted starting in 2006 in Stockton, Calif., and in 2009 in Roosevelt, Wash. In 2007, the first fruit from trial growing fields were then evaluated.

Throughout the aforementioned trials and various asexual propagations, the tree and fruit produced thereby were compared to the originally discovered plant. All characteristics of the original tree, and its fruit were established, and appears to have been transmitted to the aforementioned succeeding generations.

SUMMARY OF THE INVENTION

The present cherry tree variety 'SMS-16-CA 2014-16' is an early ripening selection which matures 3 to 7 days after the 'PC 7146-23' cherry tree variety (U.S. Plant Pat. No. 8,545, hereinafter referred to by its trade name 'Chelan') in the Roosevelt, Wash. area; and 5 to 8 days later than the 'Brooks' cherry tree (U.S. Plant Pat. No. 6,676) in the Stockton, Calif. area. 'SMS-16-CA 2014-16' is a distinct cherry tree because it is larger and more productive than either 'Chelan' or 'Brooks' cherry trees when grown under similar environmental conditions. It is believed that the self-fertile alleles $S_1S_4'$ help to insure regular cropping as compared with the self-infertile cultivars 'Chelan' and 'Brooks' cherry trees, and which require cross-pollination. In California, notably, the 'SMS-16-CA 2014-16' produces fruit which has a smooth suture line as compared with many other cherry tree varieties which produce fruit in California. In growing fields and during seasons prone to produce fruit which have the characteristic which is called "deep suture", the new variety 'SMS-16-CA 2014-16' produced fruit which showed little of this phenomenon. During commercial packing there is a minimum tolerance for this condition. Consequently many cherries are graded into a lower category or eliminated from packing as a result of "deep suture". This often results in a lower price received for the lot of cherries. The organoleptic qualities of the new fruit are superior to the fruit produced by either the 'Chelan' or 'Santina' cherry trees. These qualities are highly appreciated by those consuming the fruit. The fruit size can average about 25-28 mm in diameter as compared with 22-24 mm in diameter as displayed by the fruit produced by the 'Chelan' cherry tree even though the crop is much larger. Many fruit can be in the 32 to 36 mm diameter range. The cherry of the new variety is dark red (CTIFL color codes 4 and 5) at harvest, and a deep purplish color (CTIFL 6 color code) at full maturity.

The firmness of the fruit is comparable to the fruit produce by the 'Chelan' cherry tree with a tendency toward being slightly less firm because of the large cropping potential of the variety.

The present, new variety is distinguishable from the 'SC3-35' cherry tree variety (the parent), in view of its higher and more regular fruit production per tree, when compared to the fruit production of the 'SC3-35' cherry tree. Further, the present, new variety is distinguishable from the 'SC3-35' cherry tree in view of the fruit it produces, which possesses a larger fruit size than the fruit produced by the 'SC3-35' cherry tree. Still further, the present, new variety is distinguishable from the 'SC3-35' cherry tree (the parent) in view of the fruit it produces, which possesses an earlier ripening date than the fruit produced by the 'SC3-35' cherry tree. Moreover, the present, new variety is distinguishable from the 'SC3-35' cherry tree (the parent) in view of the fruit it produces, which possesses improved stem length relative to the fruit produced by the 'SC3-35' cherry tree.

BRIEF DESCRIPTION OF THE DRAWINGS

The accompanying drawings, which are provided are color photographs of the new cherry tree variety.

Figure 1:
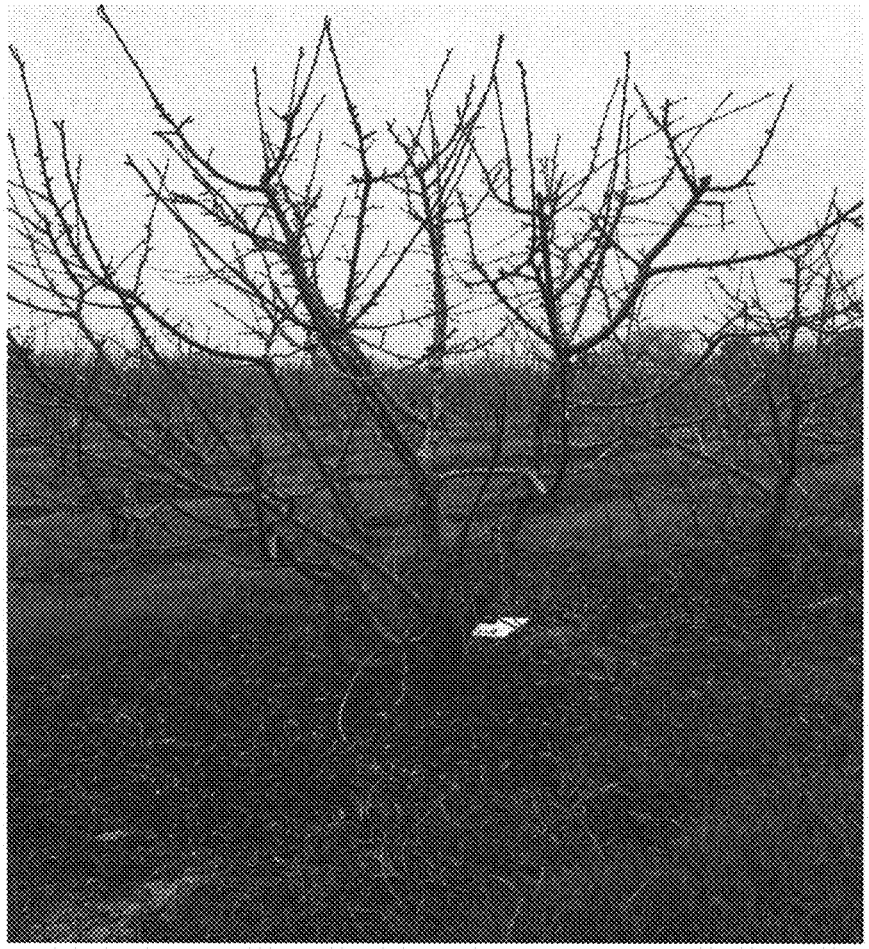
FIG. 1 depicts the original tree at full dormancy. This photograph depicts the original tree at 10 years of age.
Figure 2:
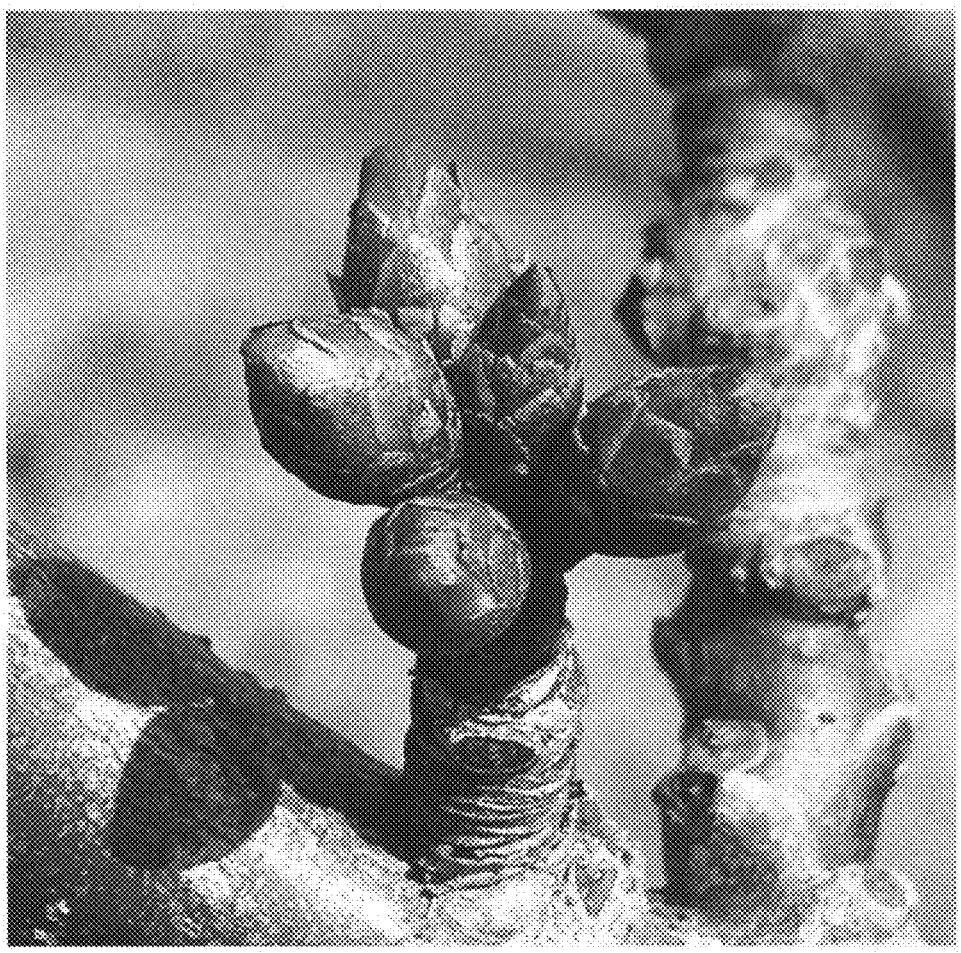
FIG. 2 depicts the semi-dormant fruiting spur of the new variety of cherry tree.
Figure 3:
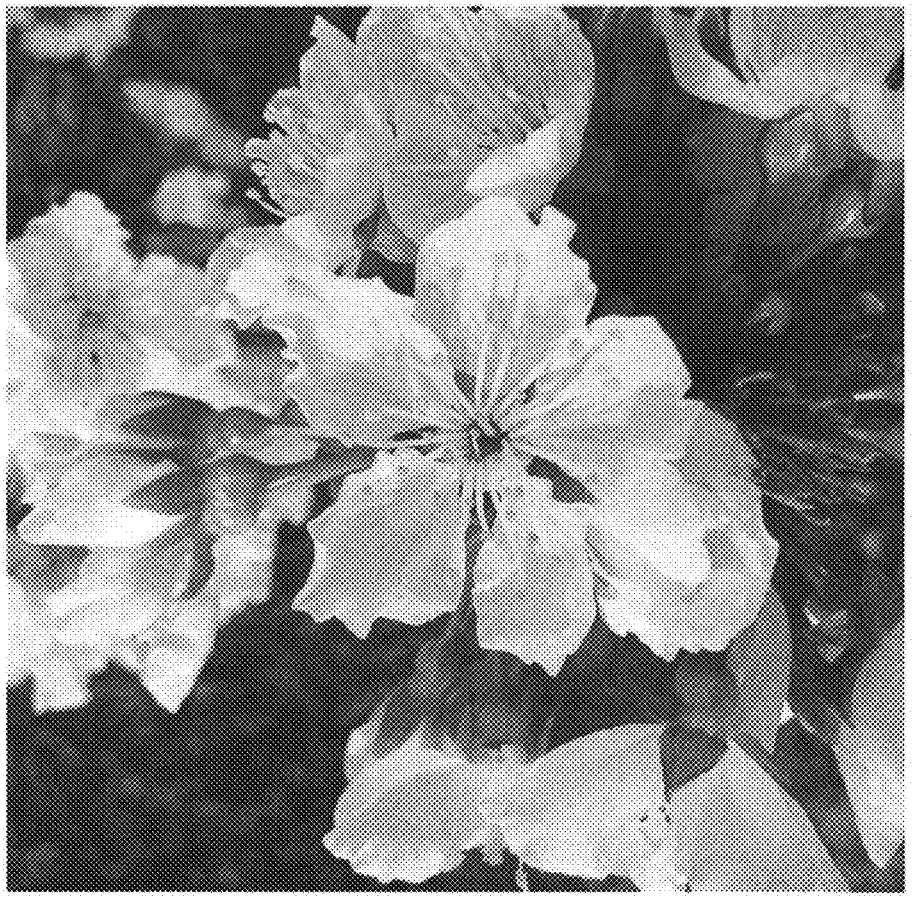
FIG. 3 depicts the flowering and blossom characteristics of the new variety of cherry tree.

The colors in these photographs are as nearly true as is reasonably possible in a color representation of this type. Due to chemical development processing, printing and the like, the leaves, fruit, flowers, and other parts of the plant, which are depicted in the enclosed photographs may, or may not be accurate, when compared to the actual specimens. For this reason future color references should be made to the color plates (Royal Horticulture Society 4th Edition 2001) and the description provided hereinafter.

NOT A COMMERCIAL WARRANTY

The following detailed description has been prepared solely to comply with the provisions of 35 U.S.C. §112, and does not constitute a commercial warranty (either expressed or implied), that the present variety will, in the future, display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety

DETAILED DESCRIPTION

Referring more specifically to the pomological details of this new and distinct variety of cherry tree, the following has been observed during the eleventh growing season, and under the ecological conditions prevailing at the orchard of the inventor which is located near Lodi, Calif. All major color code designations are by reference to The R.H.S. Colour Chart (Fourth Edition, 2001) provided by The Royal Horticultural Society of Great Britain. Common color names are also occasionally used.

Tree:

*Size*.—Based upon the current age of the tree, (11 years old) and the previous rootstock employed, the observed tree is considered moderate in size, about 10.5 feet tall; and 7 feet in diameter.

Vigor: Considered moderate for the species.

Branching habit: Upright and spreading.

Branching strength: Considered medium.

Density: Considered moderate.

Tree form: The present tree is trained to a modified open-vase form.

Hardiness: The present tree is considered hardy for the Roosevelt, Wash. area, and the region of Stockton, Calif.

Production: Considered moderate in precocity, and further typically produces flowers in the third growing season, and a crop yield in the fourth growing season of about 35-40 pounds of fruit per tree.

Bearing: Annual.

Trunk:

*Generally*.—As measured at the time bloom has a diameter when measured at a distance of 30 cm above ground of about 30.5 cm.

Bark texture: Smooth between the observed lenticels.

Bark color: Grey-purple (RHS N187A).

Lenticels:

*Generally*.—Numerous and prominent. The lenticel length averages about 20.7 mm. The lenticel width averages about 3.4 mm. The number of lenticels averages 7 lenticels per 9 square centimeters of surface area. The center color of each lenticel is grey-orange (RHS 165B); and the outer color of each lenticel is grey-white (RHS 158D).

Branches: The branches as described, below were measured at harvest maturity.

Scaffold branches: Texture-Smooth with numerous large lenticels being present.

Scaffold branch size: The Diameter of these branches when measured at a distance of 30 to 65 cm from trunk union ranges from 4.5 to 8 mm, with an average diameter of about 5.5 cm. Crotch Angle- This characteristic ranges from 30 to 60 degrees when measured from a horizontal plane.

Branch color: Grey-purple (RHS 165B).

Lenticels:

*Generally*.—Numerous and variable, and typically averaging 6 per sq. cm. The average lenticel length is about 0.24 mm; and the average lenticel width is less than about 0.2 mm. Lenticel Color: Grey-orange (RHS 165B).

2nd year fruiting branches:

*Texture*.—Smooth.

Diameter: Second year fruiting branches range in size from 4.9 mm to 8.4 mm when measured at the mid-point of growth.

Color: Second year fruiting branches have a grey-orange color (RHS 176A).

Lenticels:

*Generally*.—Few in number, and averaging 4 per running cm of length.

*Shape*.—Typically round in shape, and further range in size from about 1.0 to 1.6 mm in diameter with some being elongated, and averaging about 1.0 mm by 2.0 mm.

*Lenticel color*.—Grey-orange (RHS 164D).

Current year branches:

*Surface texture*.—Smooth.

Current year branch size:

*Average length*.—About 47 cm; Average width about 7.1 mm when measured about half way along the length thereof.

Current year branch color: Grey-orange (RHS 166A).

Internode length: This dimension ranges from about 3.3 cm to 4.9 cm. with an average length of 4.0 cm.

Lenticels:

*Numbers*.—Few, and averaging 4 per running cm of length.

*Shape*.—Small, and round, and ranging in size from about 0.8-0.9 mm. in diameter; Lenticel color: Grey-orange (RHS 164D).

Flower buds: As described hereinafter were measured at full bud swell.

Spur length: Variable, and ranging in size from 5 mm to 11 mm, with an average length of about 8 mm.

Bud shape: Acute.

Number of buds per fruiting spur: Typically 5, however, the numbers of buds can range in number from 3-7.

*Bud length*.—Averages, about 8.4 mm.

*Bud diameter*.—On average about 4.4 mm.

*Bud scale color*.—Grey-purple (RHS 187A).

Leaves: All measurements as provided, hereinafter, were taken from the mid-point of actively growing current season's growth at the time of harvest maturity.

Blade:

*Size*.—Medium-large for the species, and averaging about 13.7 cm in length; 6.1 cm in width; and further having a thickness of about 0.2 mm.

Surface texture:

*Upper surface*.—Considered smooth and leathery.

*Lower surface*.—Considered smooth and leathery, and further displaying a vein protruding above the surface.

Leaf tip: Considered more cuspidate than acuminate.

Leaf base: Obtuse.

Leaf form/shape: Elliptical.

Marginal Form: Doubly serrate with one point being less prominent than the other.

Blade color:

*Upper surface*.—Green (RHS 137A).

*Lower surface color*.—Green (RHS 138A).

Midvein:

*Generally*.—Considered medium-large; and averaging 1.0 mm in diameter when measured at the mid-point of blade. Midvein Color is yellow-green (RHS 150D).

Petiole: On average the petiole is about 4.5 cm in length; and about 1.7 mm in diameter when measured at its mid-point; upper surface color of the petiole is grey-orange (RHS 164B); lower surface color is yellow-green (RHS 150D. A 0.5 mm depth groove runs the full length of upper surface.

Leaf glands:

*Generally*.—Present, kidney shaped, and averaging about 2.7 mm in length, and 1.6 mm in width.

*Leaf gland numbers*.—Variable and ranging from 2-3, and mostly two per petiole. The leaf glands are generally located within 0.5 cm from the blade base.

*Leaf gland position*.—Generally alternate in position.

*Leaf gland color*.—Grey-purple (RHS 185A).

Leaf stipules: Not present.

Flowers:

*Generally*.—The bloom stands out, and does not drupe.

First bloom: March 3-March 6, based upon a 3 year average.

Full bloom: March 14-March 16, based upon a 3 year average.

Size:

*Bloom diameter*.—When fully open each flower averages about 33.5 mm in diameter, and is further considered open.

Bloom count: Numerous spurs are present on branches over two-years-old. Buds bearing flowers are numerous along the spurs and within each bud there are typically a range of from 3-4 blossoms (flowers) per bud, and mostly 3.

Petals:

*Numbers*.—Five.

*Color*.—White and occasionally somewhat translucent; average length is about 15.8 mm; average width is about 15.7 mm. The Petal shape is round, the petal base is obtuse, the petal margin is sinuate, and the petal apex is rounded.

Flower petal arrangement: Free to intermediate.

Nectary color: Yellow-green (RHS 154B).

Stamens:

*Filaments*.—The average number per bloom is 32.

*Color*.—White (RHS 155C). Average filament length is 6.4 mm.

Anther:

*Shape*.—Kidney shaped with an average size of 0.2 mm in width, and a length of about 0.4 to 0.7 mm.

Pollen:

*Quantity*.—Abundant.

*Pollen color*.—Grey-orange (RHS 163C).

Carpel:

*Style*.—The average length is about 11.0 mm; and the style color is yellow-green (RHS 149D).

Stigma:

*Shape*.—Clubbed and considered oval in shape.

*Stigma diameter*.—This characteristic ranges in size from 0.5 to 0.8 mm.

*Stigma color*.—Yellow-green (RHS 149C).

Sepals:

*Numbers*.—Five; deltoid in shape, and generally laid back over the thalamus. The average base width is about 4.4 mm; the average length is about 6.4 mm; the color is yellow-green (RHS 146C); and further has outside tip highlights that are grey-red (RHS 181A).

Peduncle:

*Size*.—The average length is 13.3 mm; the average diameter when measured at mid-length is about 1.0 mm; and the color is yellow-green (RHS 144A).

Thalamus:

*Size*.—The average depth is about 6.1 mm; and the average width at the opening is about 3.6 mm.

*Shape*.—Urn shaped.

*Thalamus color*.—Yellow-green (RHS 144B).

Sepals: Generally: 5 in number. The sepal shape is deltoid, and the Sepals are folded back over the thalamus and oriented at a 45° angle. The sepal length averages about 6.3 mm, and the base width averages about 4.3 mm. Upper and lower surface color is yellow-green (RHS 144A); the undersurface has tip highlights which are considered grey-purple (RHS N186D).

FRUIT

Maturity when described: The harvest maturity of the new variety in 2015 was May 9-12. The three year harvest date average was May 11.

Fruit size: Considered medium for the species, and having an average apical diameter of about 24.3 mm; and an average axial diameter of about 27.2 mm.

Fruit form:

*Generally*.—Oblate, and having uniform sides. The fruit is somewhat blunted.

Fruit suture: The suture is very distinct on the back side only, and is typically flush with sides. Suture width- About 0.3 mm.

Fruit base: Uniform and flat to reniform in shape, and having an average width of about 13.3 mm; and an average depth of about 6.4 mm. Approximately 30% of the mature fruit have two ridges which form where the suture meets the base. The aforementioned ridges range in size from about 0.4-1.0 mm in height, and are further about 1.0 mm in width. There is some variation in larger fruit samples. However, this variation is not distinctive of the present variety.

Apex:

*Shape*.—Rounded and ending in a distinct depression having a depth of about 1.0 to 1.5 mm, and which is further marked by a russeted dot which is about 1.5 to 2.0 mm in diameter.

Peduncle: The length ranges from about 26.2 to 36.3 mm, and further has an average length of about 30.6 mm.

*Peduncle diameter*.—When measured at the mid-point is about 1.4 mm; peduncle color is green (RHS 138C).

Skin:

*Thickness*.—Considered thin, about 0.05 to 0.08 mm.

Surface texture: The surface texture is smooth, and clear, and melts in the mouth.

Lenticels, amount on fruit skin: Few.

Tenacity: Considered tenacious to the flesh. Typically a thin layer of flesh is removed when the fruit is peeled.

Tendency to crack: Not observed following rain events.

Down: Wanting.

Figure 4:
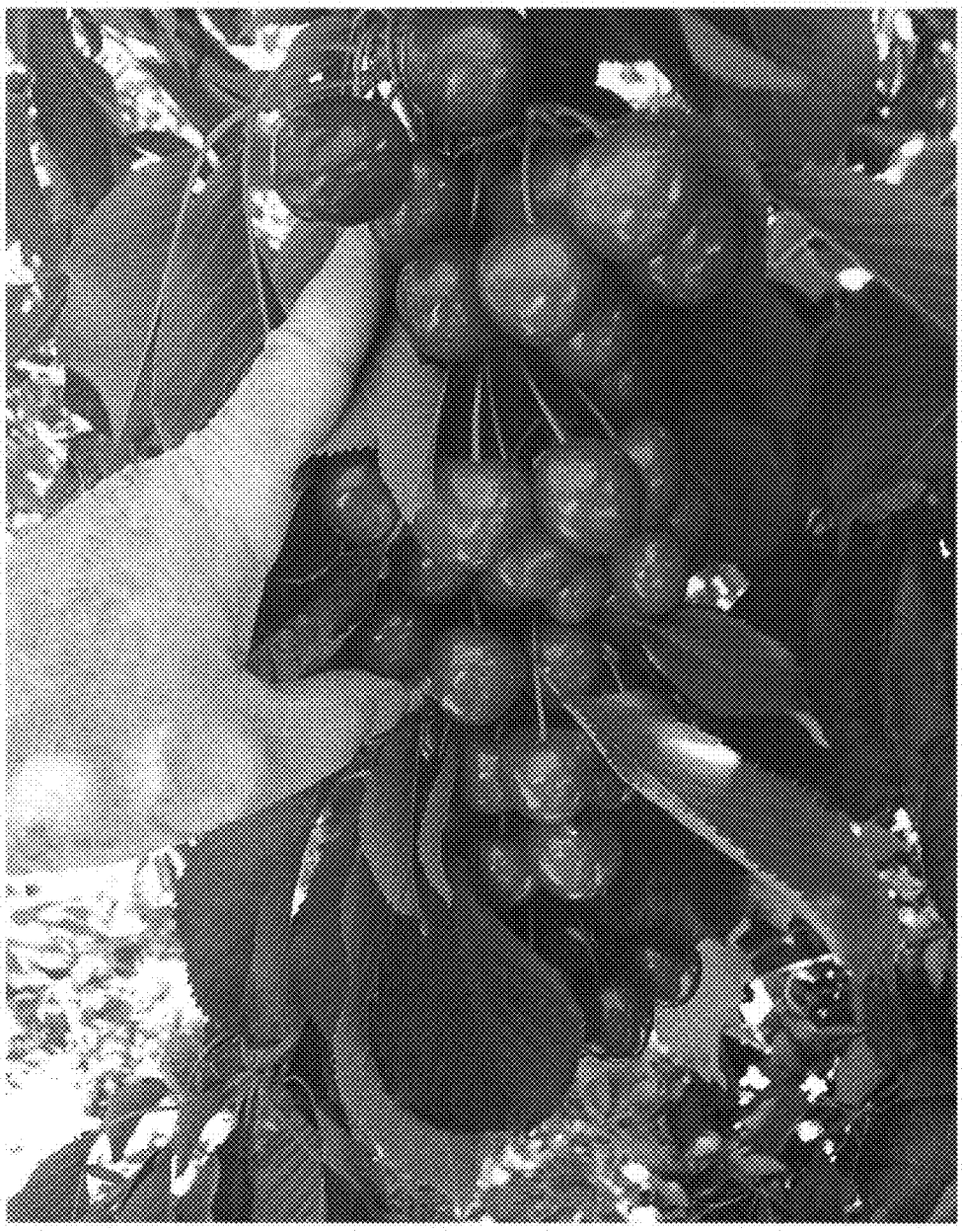
FIG. 4 depicts the appearance of the fruit and foliage of the new variety of cherry tree at harvest maturity.

Color: Considered uniform, purple, (RHS 79A), when sufficiently mature. FIG. 4 as provided shows the fruit at harvest maturity, and does not depict the fruit as would be seen when received by a consumer.

Flesh:

*Color*.—Purple (RHS N79B) with purple striping (RHS N79C).

Pit cavity color: Purple (RHS N79A).

Flesh texture:

*Generally*.—Firm, snappy and lightly fibrous.

Fibers: Generally-Considered moderate in number.

Pit tenacity: Considered moderate around the suture line, and light to none elsewhere around pit.

Ripens: Evenly.

Flavor: Sweet and sub-acid.

Aroma: Slight and cherry-like.

Eating quality: Excellent.

Stone: Type: Considered a weak clingstone.

Size: Medium; with an average length of about 10.8 mm when measured from the base to the apex. The stone is about 7.4 mm wide when measured shoulder-to-shoulder; and about 9.3 mm wide when measured suture-to-suture.

Form: Narrowly elliptical.

Base:

*Shape*.—Rounded.

Apex:

*Shape*.—Rounded.

Sides: Considered equal.

Surface texture: Considered smooth.

Ventral edge:

*Generally*.—The suture is mostly sunken, and is subtended by two low ridges which converge basally, and apically, and that averages about 4.6 mm width at the mid-point. These ridges are again subtended by two partial ridges extending from the base to ⅔ the distance to the apex; and are further 2.4 mm wide at their widest point.

Dorsal edge: Generally a distinct, smooth, slightly raised ridge which extends from the base to the apex, and which further, is about 0.4 mm high; and about 0.2 mm in width.

Stone color: Gray-orange (RHS 165D).

Tendency to split: Not observed.

Kernel:

*Shape*.—Considered obtuse.

Kernel base:

*Shape*.—Rounded.

Kernel apex:

*Shape*.—Acute.

Kernel size: The length of the kernel ranges from about 6.9 to 7.4 mm. The width of the kernel ranges from about 4.4 to 5.0 mm. The thickness of the kernel ranges from about 2.8 to 3.8 mm.

Kernel color: Grey-orange (RHS 163A).

Kernel taste: Bitter, and almond like.

Kernel viability: About 11% of the kernels did not develop. Viable kernel germination is unknown.

Pollination requirement: Considered Self-fertile (alleles $S_1S_4'$).

Use: Considered an early to early mid-season premium fresh market fruit.

Keeping quality: The fruit of the new variety appears to have adequate keeping quality for 10-14 days with forced air cooling at 33° F., and high relative humidity. However, storage tests have been limited.

Resistance to insects and diseases: The new variety shows no unusual susceptibility nor resistance to any diseases and/or plant or fruit pests of sweet cherry trees which are grown in the geographical vicinity of Roosevelt, Wash. or Stockton, Calif. where new variety was tested.

Shipping quality: Small scale tests have not revealed any special problems with pitting or softening of the fruit.

Variance in botanical details: The new variety 'SMS-16-CA 2014-16' exhibits the above described characteristics when it is grown near Stockton, Calif. and Roosevelt, Wash., respectively. It is expected that differences may occur when the new variety is grown in geographical areas which have different growing conditions.

Having thus described and illustrated my new variety of cherry tree, what I claim as new and desire to secure by plant Letters Patent is:

1. A new and distinct variety of cherry tree, substantially as illustrated and described, and which is characterized, at least in part, by producing fruit having a very large size; an early ripening time; is highly productive, and which further has symmetrically shaped fruit when grown under the ecological conditions prevailing in the states of California and Washington, and wherein the mature fruit displays little or no indentation along the suture line.

* * * * *